(12) United States Patent
Kölbel

(10) Patent No.: US 10,610,394 B2
(45) Date of Patent: Apr. 7, 2020

(54) SYSTEMS AND METHODS FOR USING PERFLUOROCARBONS TO REMOVE GASES FROM MEDICAL DEVICES

(71) Applicant: MOKITA MEDICAL GmbH i.Gr., Hamburg OT (DE)

(72) Inventor: Tilo Kölbel, Hamburg (DE)

(73) Assignee: Mokita Medical GmbH, Berlin (DE)

( * ) Notice: Subject to any disclaimer, the term of this patent is extended or adjusted under 35 U.S.C. 154(b) by 200 days.

(21) Appl. No.: 15/644,705

(22) Filed: Jul. 7, 2017

(65) Prior Publication Data

US 2017/0367861 A1    Dec. 28, 2017

Related U.S. Application Data

(63) Continuation-in-part of application No. 15/234,572, filed on Aug. 11, 2016, now Pat. No. 10,278,847.

(Continued)

(51) Int. Cl.
*A61F 2/966* (2013.01)
*A61F 2/24* (2006.01)
(Continued)

(52) U.S. Cl.
CPC ............ *A61F 2/966* (2013.01); *A61F 2/2427* (2013.01); *A61F 2/95* (2013.01); *A61F 2/958* (2013.01);
(Continued)

(58) Field of Classification Search
CPC .................................. A61F 2/95; A61B 90/70
See application file for complete search history.

(56) References Cited

U.S. PATENT DOCUMENTS 4,875,480 A    10/1989  Imbert
5,350,359 A     9/1994  Shaffer et al.
(Continued)

FOREIGN PATENT DOCUMENTS

EP    0493677 B1    3/1998
EP    1779818 A2    5/2007
(Continued)

OTHER PUBLICATIONS

Celik, Atac and Ozcan Ozeke, Management of Coronary Air Embolism During Coronary Stenting, Kardiologia Polska, 2010; 68, 6: 716-718, Gaziosmanpasa University, Tokat, Turkey, www.kardiologiapolska.pl.

(Continued)

*Primary Examiner* — Ashley L Fishback
(74) *Attorney, Agent, or Firm* — William A. English; Vista IP Law Group LLP

(57) ABSTRACT

Systems and methods are provided for removing air from a medical device, such as a stent-graft and/or its delivery device. In an exemplary embodiment, the stent-graft or its delivery system or both are exposed to perfluorocarbon, by immersing the stent-graft or flushing the delivery device to remove air from the stent-graft. Optionally, the stent-graft and/or delivery system may be flushed multiple times, e.g., with perfluorocarbon before or after flushing with carbon dioxide, saline, a bio-inert gas, and the like. Thereafter, the stent-graft may be introduced into a patient's body and deployed at a target location, such as the site of an abdominal aortic aneurysm.

17 Claims, 3 Drawing Sheets

Related U.S. Application Data

(60) Provisional application No. 62/203,624, filed on Aug. 11, 2015.

(51) Int. Cl.

| | | |
|---|---|---|
| *B01D 53/14* | (2006.01) | |
| *A61M 25/10* | (2013.01) | |
| *A61F 2/958* | (2013.01) | |
| *A61F 2/95* | (2013.01) | |
| *A61M 5/36* | (2006.01) | |
| *A61M 39/22* | (2006.01) | |
| *A61F 2/01* | (2006.01) | |
| *A61B 17/12* | (2006.01) | |
| *A61F 2/07* | (2013.01) | |
| *A61B 17/00* | (2006.01) | |

(52) U.S. Cl.
CPC ........ *A61M 5/36* (2013.01); *A61M 25/10182* (2013.11); *B01D 53/14* (2013.01); *A61B 17/1214* (2013.01); *A61B 17/12118* (2013.01); *A61B 17/12131* (2013.01); *A61B 2017/00526* (2013.01); *A61B 2017/1205* (2013.01); *A61F 2/01* (2013.01); *A61F 2/07* (2013.01); *A61F 2/2466* (2013.01); *A61F 2002/011* (2013.01); *A61F 2002/9517* (2013.01); *A61M 39/225* (2013.01); *A61M 2025/1077* (2013.01); *A61M 2210/12* (2013.01); *A61M 2210/127* (2013.01)

(56) References Cited

U.S. PATENT DOCUMENTS

| | | |
|---|---|---|
| 5,427,104 A | 6/1995 | Briend et al. |
| 5,800,375 A | 9/1998 | Sweezer et al. |
| 5,817,046 A | 10/1998 | Glickman |
| 5,865,789 A | 2/1999 | Hattler |
| 6,106,497 A | 8/2000 | Wang |
| 6,117,102 A | 9/2000 | Schwartz et al. |
| 6,152,141 A | 11/2000 | Stevens |
| 6,241,699 B1 | 6/2001 | Suresh et al. |
| 6,534,002 B1 | 3/2003 | Lin et al. |
| 6,821,263 B2 | 11/2004 | Lenker et al. |
| 6,823,879 B2 | 11/2004 | Fillipi |
| 7,503,904 B2 | 3/2009 | Choi |
| 7,875,067 B2 | 1/2011 | Von Oepen et al. |
| 7,955,370 B2 | 6/2011 | Gunderson |
| 8,025,691 B2 | 9/2011 | Carter et al. |
| 8,480,627 B2 | 7/2013 | Christiansen |
| 8,628,490 B2 | 1/2014 | Yacoubian et al. |
| 8,740,976 B2 | 6/2014 | Tran et al. |
| 8,828,072 B2 | 9/2014 | Hoffman et al. |
| 9,038,564 B2 | 5/2015 | Fiorini et al. |
| 9,131,926 B2 | 9/2015 | Crisostomo et al. |
| 9,333,077 B2 | 5/2016 | Peter |
| 2002/0087119 A1 | 7/2002 | Parodi |
| 2002/0138126 A1* | 9/2002 | Camrud ............... A61F 2/95 623/1.11 |
| 2004/0171937 A1 | 9/2004 | Adams |
| 2007/0181157 A1 | 8/2007 | Dadourian |
| 2009/0005852 A1 | 1/2009 | Gittings et al. |
| 2009/0018486 A1 | 1/2009 | Goren et al. |
| 2010/0318114 A1 | 12/2010 | Pranevicius et al. |
| 2013/0079858 A1 | 3/2013 | Helkowski et al. |
| 2014/0100645 A1 | 4/2014 | Mayle et al. |
| 2014/0243873 A1 | 8/2014 | Franklin |
| 2014/0277403 A1 | 9/2014 | Peter |
| 2015/0209557 A1 | 7/2015 | Tal et al. |
| 2015/0297381 A1 | 10/2015 | Essinger et al. |
| 2015/0374401 A1 | 12/2015 | Guggenheimer et al. |
| 2017/0042712 A1 | 2/2017 | Kolbel |
| 2017/0143446 A1 | 5/2017 | Kolbel |
| 2018/0110640 A1* | 4/2018 | Brister ............... A61F 5/01 |

FOREIGN PATENT DOCUMENTS

| | | |
|---|---|---|
| WO | 9203205 A1 | 3/1992 |
| WO | 02054990 A2 | 7/2002 |
| WO | 03002020 A2 | 1/2003 |
| WO | 2006089517 A1 | 8/2006 |

OTHER PUBLICATIONS

Kölbel, Tilo, et al., Carbon Dioxide Flushing Technique to Prevent Cerebral Arterial Air Embolism and Stroke During TEVAR; Journal of Endovascular Therapy, 2016, 1-3, www.jevt.org.

* cited by examiner

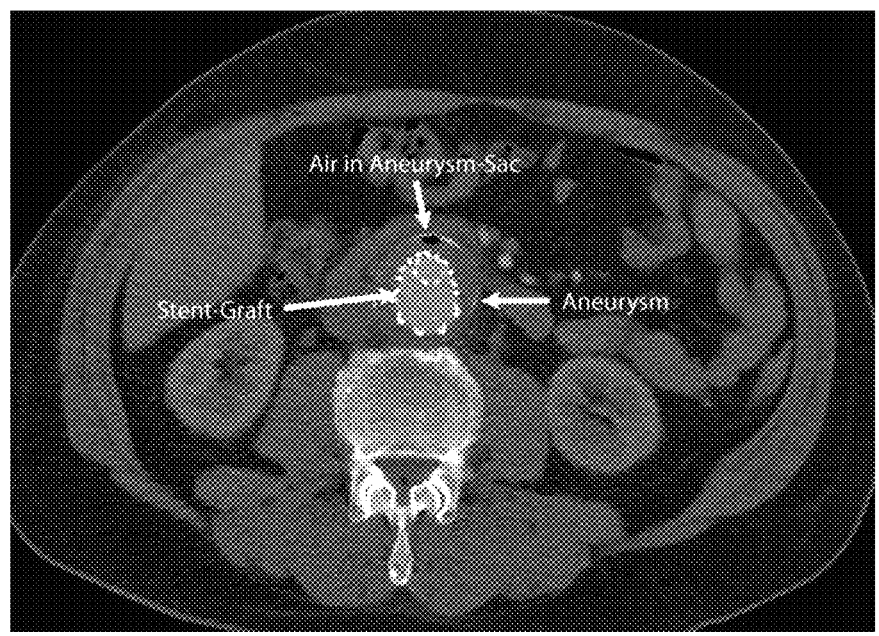
FIG. 1
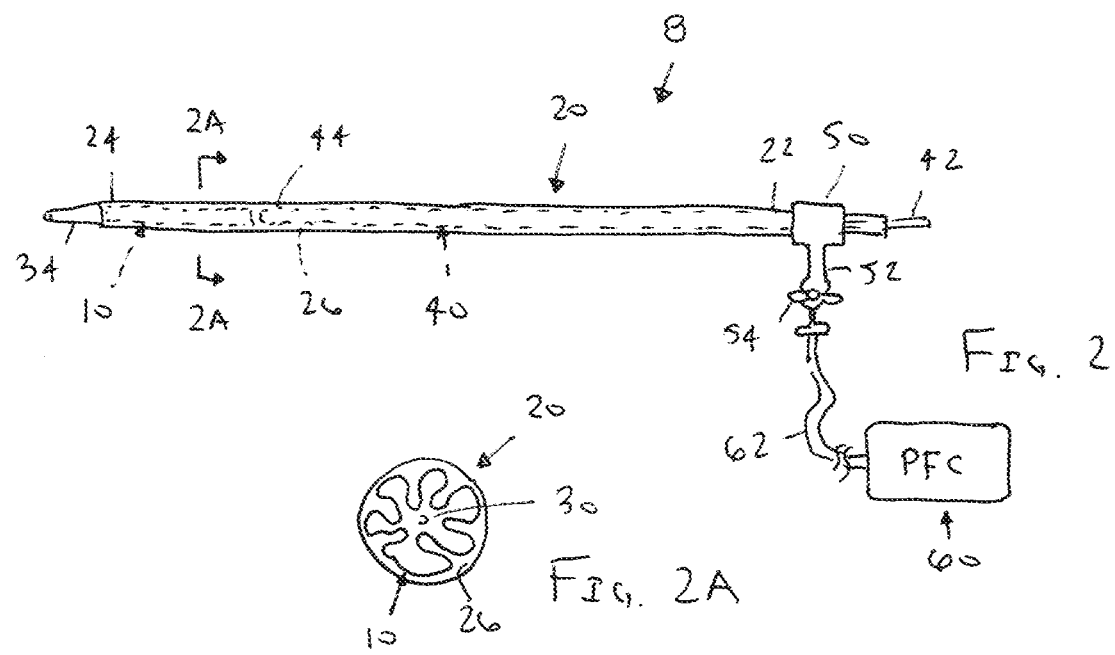

SYSTEMS AND METHODS FOR USING PERFLUOROCARBONS TO REMOVE GASES FROM MEDICAL DEVICES

RELATED APPLICATION DATA

The present application is a continuation-in-part of co-pending application Ser. No. 15/234,572, filed Aug. 11, 2016, which claims benefit of provisional application Ser. No. 62/203,624, filed Aug. 11, 2015, the entire disclosure of which is expressly incorporated by reference herein.

FIELD OF THE INVENTION

The present invention relates to devices, systems, and methods for removing gasses from medical devices, e.g., stent-grafts; stents; vascular and neurovascular coils; covered and uncovered occluders; embolic protection devices and filters; heart valves; valve repair and augmentation prostheses; other prostheses; and the respective delivery systems for such devices, before or after introduction into a patient's body, to reduce the risk of embolism, which may be formed by unwanted intravascular gas and gas composite volumes, using perfluorocarbons and or other gases and or other fluids as part of a related flushing system and method.

BACKGROUND

Endovascular aortic repair (EVAR) is a type of endovascular surgery used to treat pathology of the aorta. The most common EVAR treatment is of an abdominal aortic aneurysm, but many different types of aortic pathologies are treated by EVAR. When used to treat thoracic aortic disease, the procedure is then specifically termed TEVAR (thoracic endovascular aortic/aneurysm repair). The procedure involves placement of an expandable stent-graft within the aorta to treat the aortic disease without operating directly on the aorta. In 2003, EVAR surpassed open aortic surgery as the most common technique for repair of abdominal aortic aneurysm, and in 2010, EVAR accounted for 78% of all intact abdominal aortic aneurysm repair in the United States.

The procedure is carried out in a sterile environment under x-ray fluoroscopic guidance by a vascular surgeon, cardiac surgeon, interventional radiologist, general surgeon, or interventional cardiologist. The patient's femoral arteries are generally accessed percutaneously, e.g., with a surgical incision or direct puncture in the groin. Vascular sheaths are introduced into the patient's femoral arteries, through which one or more guide wires, catheters, and the stent-graft are introduced. The stent-graft acts as an artificial lumen for blood to flow through, thereby substantially isolating the aneurysm sac from direct blood flow and blood-pressure and thereby preventing further enlargement and rupture. The stent-graft is compressed into a catheter, introducer sheath, or other delivery system that allows the compressed stent-graft to be introduced from the femoral arteries to the intended place of deployment.

A stent-graft is typically an assembly of a fabric material and a metal frame or metal springs/stents and mounted on a catheter assembly. When introduced into the vasculature, stent-grafts are constrained to a smaller diameter to enable introduction by different techniques, such as a constraining sleeve or by loading into an introducer sheath. Stent-grafts, stents, and their catheter assemblies are typically produced, constrained, packed and, sterilized under room-air conditions. Consequently, spaces within a constraining sleeve or sheath that are not filled by the stent-graft or stent and/or the catheter assembly generally contain room air. For sterilization, the assemblies are packed in packaging, which is permeable for gas and are sterilized, e.g., using vacuum with ethyleneoxide-containing gas. The gas is removed by repeated vacuum and room air ventilation as a later step of the gas-sterilization process. Thus, when the product is delivered in its sterile packaging there is generally air present within the stent-graft assembly.

In the operating theatre, the stent-graft assemblies are unpacked from their packaging under sterile conditions. Air is removed from some stent-grafts and their catheter assemblies prior to introduction into the vasculature typically by flushing the sheath with isotonic solutions such as saline introduced through flushing ports that are part of the catheter assemblies. Stent-grafts that are constrained using a sleeve, such as the Gore TAG and cTAG device, are typically introduced into the vasculature without flushing to remove the room-air from the assembly.

It is well recognized that deployment of stent-grafts in the thoracic aorta involves a significant risk for stroke. It has been reported to be as high as 10% and is a major drawback of TEVAR.

While retrospective studies have been done, the pathomechanism of stroke as a complication of TEVAR is not well known. Generally, the main source for strokes are thought to be embolism by particles from thrombotic and atherosclerotic material adherent to the aortic wall, which is released by manipulation during deployment by wires, catheters, sheaths and the stent graft. The release of trapped gas or gas mixtures, e.g., air or nitrogen, from the stent-graft during TEVAR may form emboli and/or be a significant pathomechanism for cerebral emboli leading to stroke despite flushing techniques; however, it has been difficult to detect such event cascades since released gas or gas composites are not visible and a stroke attributed to gas embolism may only first be recognized after the patient has woken up.

The risk of air-embolism and stroke during open surgery is well known and preventive strategies have been employed, e.g., in open cardiac surgery and neuro-surgery. Preventive strategies to avoid the introduction of air within endovascular devices into the human body include extensive saline flushing to mechanically squeeze out the air, which is present in catheters, stents (uncovered metal stents), coils, and other devices prior to introduction of these devices into the patient's vasculature. Such flushing with saline generally works well in these applications as air may be removed almost completely; therefore, such flushing is generally part of the instructions for use of these devices.

With stent-grafts (prosthetic vascular grafts supported by metal stents), flushing with saline solution may not work well to remove air prior to introduction into the body. However, it is the method that is widely recommended and used today in most procedures. Because stent-grafts are combinations of stents with a fabric-covering, traditional mechanical flushing with saline may not work well because the fabric significantly hampers the ability to completely drive out the air. Also, factors like the degree of compression may influence the amount of "trapped air."

Another factor is the presence of side-branches and other advanced tools in modern stent-grafts and their delivery-systems, which may create additional pockets where air may be compressed during flushing, but not squeezed out. During the procedure, the trapped air may then be released during intravascular deployment but may not be visually recognized during the procedural step since air is not typically visible under fluoroscopy, which is generally used for such procedures. The released air may become visible on postoperative CT-scans after EVAR for abdominal aortic aneurysms in the aneurysm-sac days after the procedure, e.g., as shown in FIG. 1. Such occurrences are largely ignored because this air does not seem to cause much harm and is expected to be resorbed within weeks.

Trapped air may also be released when stent-grafts are deployed in segments of the aorta, which are close to brain-supplying arteries or the aortic trunk vessels, e.g., the innominate artery, left common carotid artery, and left subclavian artery. When such trapped air is released, there is a risk of air embolization into the brain. Thus, insufficient removal of air from stent-grafts and/or their delivery systems before they are introduced into the vasculature may be a significant source of stroke during TEVAR. Additionally, a related situation applies if stent-grafts are released close to the coronary arteries, which gives rise to a risk for myocardial infarction due to air-embolization into the coronary arteries.

Air is also known to be released from other medical devices used in neuroradiological procedures. For example, stents and coils and their delivery-assemblies, which are introduced in the arteries of the brain, may also contain air, which may potentially cause damage in the brain. In addition, there is significant stroke risk associated with transcatheter aortic valve implantation ("TAVI") and current measures, e.g., introducing filters, deflectors, and the like into the patient's vasculature during the procedure, may be ineffective at capturing air or other unwanted gases.

Accordingly, devices and methods that facilitate removing air or other gases from medical devices, particularly stent-grafts, stents, coils and their delivery systems, to reduce the risk of embolism would be useful.

SUMMARY

The present invention is directed to devices and methods for removing gases from medical devices, e.g., stent-grafts; stents; vascular and neurovascular coils; covered and uncovered occluders; embolic protection devices and filters; heart valves; valve repair and augmentation prostheses; other prostheses; and the respective delivery systems for such devices, before or after introduction into a patient's body, to reduce the risk of embolism, which may be formed by intravascular gas or gas composite volumes. As used herein, "target gas" refers to unwanted gases or gas mixtures, e.g., air, nitrogen, and the like, that may be trapped within a device and/or create a risk of embolism or stroke within a patient's vasculature and/or other locations within the body.

In accordance with one embodiment, a system is provided for flushing a medical device comprising an elongate delivery device comprising a proximal end, a distal end, a lumen extending between the proximal and distal ends, and a port on the proximal end communicating with the lumen, a prosthesis carried by the delivery device within the lumen, the system comprising a source of gas comprising one of carbon dioxide and a bio-inert gas connectable to the port for flushing the lumen with the gas to replace target gas within one or both of the prosthesis and the lumen with the flushed gas; and a source of perfluorocarbon solution connectable to the port for flushing the lumen with the solution to absorb the flushed gas from one or both of the prosthesis and the lumen into the solution.

In accordance with another embodiment, a method is provided for preparing a medical device that includes flushing the medical device with a gas to displace target gas from the medical device; and thereafter, flushing the medical device with perfluorocarbon to dissolve and remove the flushed gas. Such flushing may reduce the risk of air or other gases entering the device and/or otherwise being introduced into a patient's body during use of the device.

In accordance with still another embodiment, a system is provided for flushing target gas from a medical device that includes an elongate delivery device comprising a proximal end, a distal end, a lumen extending between the proximal and distal ends, and a port on the proximal end communicating with the lumen; a prosthesis carried by the delivery device within the lumen; and a source of perfluorocarbon solution connectable to the port for flushing the lumen with the solution to remove target gas from one or both of the prosthesis and the lumen.

In accordance with yet another embodiment, a method is provided for removing target gas from a medical device that includes providing a source of perfluorocarbon; and exposing the medical device to perfluorocarbon from the source of perfluorocarbon to remove target gas, e.g., trapped air, from the medical device.

In accordance with still another embodiment, a method is provided for removing target gas from a medical device that includes flushing the medical device with perfluorocarbon; and separately flushing the medical device with one or more of saline, carbon dioxide, and a bio-inert gas.

In accordance with another embodiment, a method is provided for removing target gas from one or both of a stent-graft and its delivery system that includes contacting the stent-graft or its delivery system or both with a perfluorocarbon for a time sufficient to remove a quantity of target gas from the stent-graft, and thereafter introducing the stent-graft into a patient's body. A perfluorocarbon solution may, not just mechanically drive out target gas within the stent-graft, but may absorb the target gas, e.g., trapped air, present in the stent-graft and/or its delivery system, thereby reducing the risk of an air embolism when the stent-graft is introduced and deployed within a patient's body. For example, degassed perfluorocarbon may have a relatively high solubility for target gases, notably air or nitrogen, such that may readily dissolve the target gas to remove it from exposure within the patient's body.

In accordance with another embodiment, a method is provided for removing target gas from one or both of a stent-graft and its delivery system that includes contacting the stent-graft or its delivery system or both with an emulsion comprising one or more perfluorocarbons for a time sufficient to remove a quantity of target gas from the stent-graft, and, optionally, thereafter introducing the stent-graft into a patient's body.

In accordance with still another embodiment, a method is provided for removing target gas from one or both of a stent-graft and its delivery system that includes contacting the stent-graft or its delivery system or both with a degassed solution comprising perfluorocarbon or saline or both for a time sufficient to remove a quantity of target gas from the stent-graft, and, optionally, thereafter introducing the stent-graft into a patient's body.

In accordance with yet another embodiment, a method is provided for removing target gas from one or both of a stent-graft and its delivery system that includes contacting the stent-graft or its delivery system or both with one or both of carbon dioxide and one or more bio-inert gases, such as helium or argon, with sufficient pressure and for a time sufficient to remove a quantity of target gas from the stent-graft, and thereafter flushing the stent-graft or its delivery system or both with another flushing solution, e.g., including saline or perfluorocarbon or a degassed solution containing perfluorocarbon or saline or both for a time sufficient to remove a quantity of carbon dioxide and one or more bio-inert gases, such as helium or argon, from the stent-graft, and, optionally, thereafter introducing the stent-graft into a patient's body.

In accordance with still another embodiment, a method is provided for removing target gas from a prosthesis, e.g., a valve prosthesis, that includes immersing the prosthesis in a solution comprising perfluorocarbon for a time sufficient to remove a quantity of target gas from the prosthesis; compressing the prosthesis into a delivery configuration; and loading the compressed prosthesis into a delivery device. This method may also include flushing of the delivery-system before and/or after compression of the prosthesis with PFC or other degassed solutions in order to take up unwanted gases/air and thereby preventing embolization into body vessels.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 1 is an example of a postoperative CT-scan showing released air after implanting a stent-graft during an EVAR procedure.

FIG. 2 is a side view of an introducer sheath carrying a stent-graft showing an exemplary system for removing air from the stent-graft and introducer sheath using a source of perfluorocarbon.

FIG. 2A is a cross-section of the system of FIG. 2 taken across 2A-2A.

DETAILED DESCRIPTION OF THE EXEMPLARY EMBODIMENTS

Figure 3B:
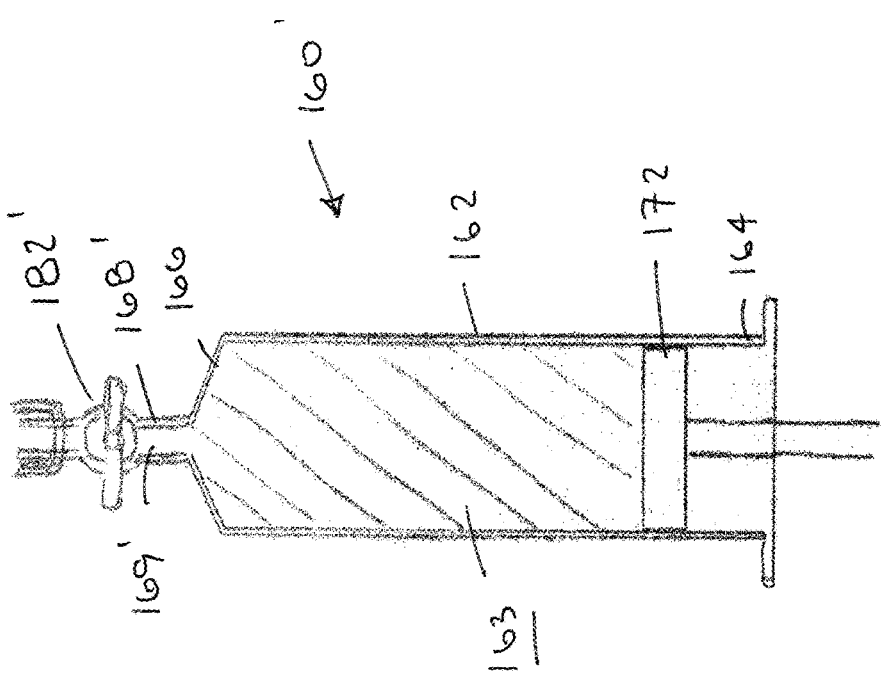
FIGS. 3A and 3B are side views of exemplary embodiments of syringe devices for delivering perfluorocarbons to flush medical devices.

Reducing the amount of air or other unwanted/target gases present in a medical device, e.g., stent-grafts; stents; vascular and neurovascular coils; covered and uncovered occluders; embolic protection devices and filters; heart valves; valve repair and augmentation prostheses; other prostheses; and the respective delivery systems for such devices, may reduce the incidence of stroke and/or other damage that may result from air embolism. In accordance with an exemplary embodiment, systems and methods are provided that use perfluorochemicals (or "PFCs") to flush medical devices, e.g., stent-grafts; stents; vascular and neurovascular coils; covered and uncovered occluders; embolic protection devices and filters; heart valves; valve repair and augmentation prostheses; other single or multiple component prostheses; and the respective delivery systems for such devices, to absorb target gas during flushing. In addition, PFCs may also be used to flush a medical device in order to remove gas formulations that have first been used to flush out unwanted target gases, which may represent sources of embolism. A perfluorocarbon liquid solution may, not just mechanically drive out air or other target gases within the medical device, but may absorb air (or other gases) present in the medical device, thereby reducing the risk of an air embolism when the medical device is introduced and/or deployed within a patient's body. For example, degassed perfluorocarbon formulations have a solubility capacity for air and other gases, such as carbon dioxide, nitrogen, and the like, such that the formulations may readily dissolve target gases to remove the target gases from exposure within the patient's body.

Any known pharmaceutical grade perfluorocarbons may be employed, such as perflubron, perfluorodecaline, perfluorotributylamine, perfluorohexane, perfluorononane, perfluoropentane, perfluorodichlorooctane, perfluoro-15-crown-5-ether, and the like. In an exemplary embodiment, the perfluorocarbons may also be employed in the form of an emulsion. Whether the perfluorocarbons are pure, dissolved in a solvent or merely suspended or dispersed within a liquid, or emulsified by using emulgators such as egg-yolk, such materials are generally defined herein as a "PFC solution." One example is perfluorotributylamine emulsified with a non-ionic surfactant, which is a polymer of polyoxyethylene and polyoxypropylene, such as Pluronic F-68 or F-127.

Perfluorocarbons have been studied in the lungs and circulation and found to be bio-inert, minimally absorbed, and free of deleterious histological cellular or biochemical effects. The molecules are too large to be metabolized and can be eliminated in the lungs, urine and feces. They also have very high vapor pressures, and therefore evaporate quickly.

Perfluorochemicals (e.g., perfluorocarbons) have already been employed in "liquid breathing," which is a form of respiration in which a normally air-breathing organism breathes an oxygen-rich liquid (a perfluorocarbon) rather than breathing air. This procedure takes advantage of the fact that a common property of this class of chemicals is a high solubility for respiratory gases. In fact, these liquids carry more oxygen, carbon dioxide, and nitrogen than blood. The perfluorocarbons are used as oxygen-carriers intravenously infused to deliver oxygen to areas damaged by embolization and to use their solubility to increase the blood's ability to take up gases within the body.

Thus, in order to reduce the incidents of stroke by reducing the amount of air present in a stent-graft and its delivery system, the stent-graft and delivery system may be immersed in or flushed with the perfluorocarbon, preferably before being introduced into the body. It will be appreciated, however, that devices may also be flushed with perfluorocarbon even after introduction into a patient's body, e.g., to absorb any air present in the device during introduction. As opposed to the prior use of perfluorocarbons to deliver oxygen to areas damaged by embolization, or the use of flushing solutions to mechanically reduce the air by pushing it out of the stent-graft, the perfluorocarbons are employed to eliminate the air from the stent-grafts and their delivery-systems before it is introduced into the body. Optionally, the perfluorocarbons may then be removed from the stent-graft and delivery system prior to introduction into the body, e.g., by flushing with saline or other solutions typically used for flushing.

In addition or alternatively, degassed solutions and degassed PFC may be used for flushing of medical devices, e.g., stent-grafts; stents; vascular and neurovascular coils; covered and uncovered occluders; embolic protection devices and filters; heart valves; valve repair and augmentation prostheses; other prostheses; and the respective delivery systems for such devices, to absorb and/or otherwise remove target gases during flushing. For example, solutions of perfluorocarbons, and other solutions, such as saline, may be degassed and thereby increase their ability to take up target gases during the flushing process. Degasification may be performed by applying vacuum to these solutions, boiling them, or by replacing an unwanted gas with another gas. After degasification of the flushing solution, the solution may be stored or otherwise maintained under atmospheric pressure, which maintains its degassed state by preventing solution of gases again.

In addition or alternatively, carbon dioxide may be used for high-pressure-flushing of medical devices, e.g., stent-grafts; stents; vascular and neurovascular coils; covered and uncovered occluders; embolic protection devices and filters; heart valves; valve repair and augmentation prostheses; other prostheses; and the respective delivery systems for such devices, by replacing the target gas with carbon dioxide. The carbon dioxide may afterwards be removed from the stent-grafts and their delivery system prior to introduction into the body, e.g., by flushing with PFC, saline or other solutions typically used for flushing. Carbon dioxide has a 22-fold higher solubility in blood compared to room air and therefore is preferred as a "trapped gas" when introduced and potentially released into the vasculature.

Turning to the drawings, FIG. 2 shows an exemplary embodiment of a stent-graft 10 carried by a delivery device 8 being flushed by a source of flushing solution 60. Generally, the delivery device 8 includes an introducer sheath, catheter, or other tubular member 20 including a proximal end 22, a distal end 24 sized for introduction into a patient's body, and one or more lumens extending therebetween, e.g., a lumen 26 within which the stent-graft 10 is loaded in a compressed or contracted condition at the distal end 24, as best seen in FIG. 2A. A handle or hub 50 may be provided on the proximal end 22 of the sheath 20 including a port 52 communicating with the lumen 26, e.g., including a valve 54 that may be selectively opened and closed.

Optionally, the delivery device 8 may include one or more additional components, e.g., a central cannula 30 also disposed within the lumen 26 and over which the stent-graft 10 may be loaded. The central cannula 30 may include an enlarged distal tip 34, e.g., to enclose a distal end of the lumen 26 and/or provide a rounded, tapered, or other atraumatic tip for the delivery device 8. The central cannula 30 may also include an instrument lumen (not shown) extending between proximal and distal ends thereof, e.g., sized to receive a guidewire or other rail, over which the delivery device 8 may be introduced into a patient's body. In addition or alternatively, the delivery device 8 may also include a pushed member 40 slidably received within the lumen 26 including a distal end 44 disposed adjacent the stent-graft 10.

For example, during use, the distal end 24 of the introducer sheath 20 (carrying the stent-graft 10) may be introduced into a patient's body, e.g., from a percutaneous entry site, and advanced to a target location, e.g., within the patient's aorta which is the site of an aneurysm (not shown). Once properly positioned, the sheath 20 may be retracted while maintaining the pusher member 30 substantially stationary to expose the stent-graft 10. The stent-graft 10 may be configured to resiliently expand within the target location automatically upon being exposed. Alternatively, the delivery device 8 may include a balloon or other expandable member (not shown), which may be inflated or otherwise manipulated to expand the stent-graft 10.

Figure 3A:
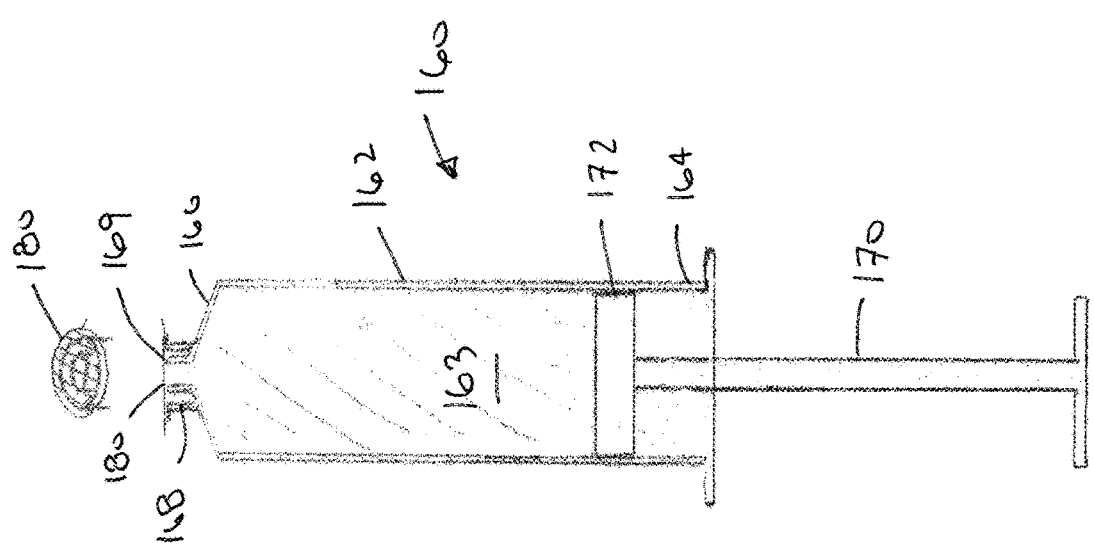

Prior to introduction of the delivery devices 8 into the patient's body, the source of flushing solution 60 may be used to flush the lumen 26 and/or stent-graft 10, e.g., to remove air. In an exemplary embodiment, the source 60 may contain a solution including one or more perfluorocarbons, as described elsewhere herein, which may be flushed into the lumen 26. For example, the solution may include an emulsion of perfluorocarbon and/or a degassed solution, as described elsewhere herein. In exemplary embodiments, the source 60 may be a syringe filled with the solution, as depicted in FIGS. 3A and 3B, or a flushing system, as depicted in FIG. 4A, a pump, or other container (not shown) that may be actuated to deliver the solution from the source 60 into the lumen 26 to flush the stent-graft 10. The source may reusable or may be a disposable, single-use device.

With continued reference to FIG. 2, the valve 54 may be initially closed to prevent air from entering the port 52 and lumen 26. Tubing 62 may be coupled between the port 52 and the source 60, e.g., using luer lock or other connectors (not shown). Once the source 60 is coupled to the port 52, the valve 54 may be opened and the solution injected into the lumen 26 to flush the stent-graft 10. For example, the solution may pass through the port 52 and lumen 26 around and/or into the stent-graft 10 and exit the distal end 24 to remove any air bubbles trapped or otherwise located within folds of the stent-graft 10 and/or otherwise within the lumen 26. Once sufficiently flushed, the valve 54 may be closed and the source 60 disconnected from the port 52. The delivery device 8 may then be introduced into the patient's body, as described elsewhere herein.

Optionally, it may be desired to provide multiple sources of flushing fluids and/or sequences of flushes to enhance removal of air and/or any other trapped gases, e.g., using the source of perfluorocarbon 60 and one or more additional sources (not shown). For example, a source of gas may be provided that contains a bio-inert gas, e.g., argon or helium, which may be coupled to the port 52, similar to the source.

In an exemplary sequence, the source of gas may be coupled to the port 52 and used to flush the lumen 26 and stent-graft 10, thereby removing and/or displacing any air therein. Thus, if any gas remains within the lumen 26 and stent-graft 10, the air will be replaced by the carbon dioxide or bio-inert gas. Thereafter, the source of gas may be disconnected, and the source of perfluorocarbon 60 coupled to the port 52 and used to flush any remaining gas within the lumen 26 and stent-graft 10. The perfluorocarbon solution may easily dissolve the carbon dioxide or bio-inert gas, thereby more effectively flushing the device 8. Optionally, the source of perfluorocarbon 60 may be disconnected, and a source of saline, e.g., degassed saline, may then be coupled to the port 52 and used to further flush the lumen 26 and stent-graft 10.

Turning to FIG. 3A, an exemplary embodiment of a syringe 160 is shown that generally includes a barrel 162 including an open proximal end 164, a closed distal end 166 including a hub 168 defining an outlet port 169, and a plunger 170 including a piston 172 slidably disposed within an interior 163 of the barrel 162. The hub 168 may include a connector, e.g., a male or female Luer fitting, for connecting the hub 168 to tubing, a flushing device, and the like (not shown). The interior 163 of the barrel 162 may be filled with PFC solution, e.g., including de-gassed PFC, as described elsewhere herein.

In addition, a seal 180 may be provided on the hub 168, e.g., attached by one or more of sonic welding, fusing, bonding with adhesive, and the like, to seal the outlet 169 and prevent air or other external gases from entering the interior 163 via the outlet 169. For example, the seal 180 may be a round panel of gas-impervious plastic, metal, or composite material that prevents external gas from entering and/or contaminating the PFC within the interior 163.

Optionally, as shown in FIG. 3B, a stop-cock 182' may be provided on a hub 168' of a syringe 160' in addition to or instead of the seal 180 shown in FIG. 3A. In either embodiment, the material for the barrel 162, piston 172, and/or other components of the syringe 160 exposed to the PFC should be formed from non-porous material that prevents external gas from entering the interior 163 to contaminate the de-gassed PFC.

During preparation, e.g., manufacturing (or even immediately before use), the syringe 160, 160' may be filled with de-gassed PFC solution, e.g., within a vacuum chamber (not shown) or other location having an absence or reduced amount of air or other gases. Once the interior 163 is filled to a desired volume, the seal 180 may be applied and/or the stop-cock 182' may be closed to isolate the PFC within the interior 173. The resulting PFC solution may not be 100% degassed PFC, but may be "substantially all" degassed PFC, e.g., about 80-99% or 95-99% degassed as a result of the loading, such that the PFC solution may have an enhanced capacity and/or may readily absorb unwanted gases, e.g., to remove target gas and prevent the gas from being subsequently released within the patient's body. The syringe 160, 160' may be processed further, e.g., sterilized and/or packaged, and provided to a user using conventional methods. Immediately, before use, the seal 180 may be removed, e.g., by tearing, puncturing, or overcoming the bond, to open the outlet 169, and the hub 168, 168' may be coupled to a device being flushed, e.g., via tubing and the like (not shown). If a stop-cock 182' is provided, the stop-cock 182' may be opened immediately before delivery, e.g., directly into a flushing device, a catheter, and the like (also not shown), as described elsewhere herein.

Turning to FIG. 4A, an exemplary embodiment of a flushing system 250 is shown that includes a PFC syringe 260, e.g., similar to the syringes 160, 160' shown in FIGS. 3A and 3B, and a source of flushing gas 280 sharing a delivery line 290. Similar to the previous embodiments, the syringe 260 includes a barrel 262 including an open proximal end 264, a closed distal end 266 including a hub 268 defining an outlet port 269, and a plunger 270 including a piston 272 slidably disposed within an interior 263 of the barrel 262. The interior 263 may be filled with one or more perfluorocarbons, e.g., de-gassed PFC solution, similar to the previous embodiments. The source 280 may include a canister or bottle 282, e.g., filled with carbon dioxide or other flushing gas, including an outlet 284.

Figure 4B:
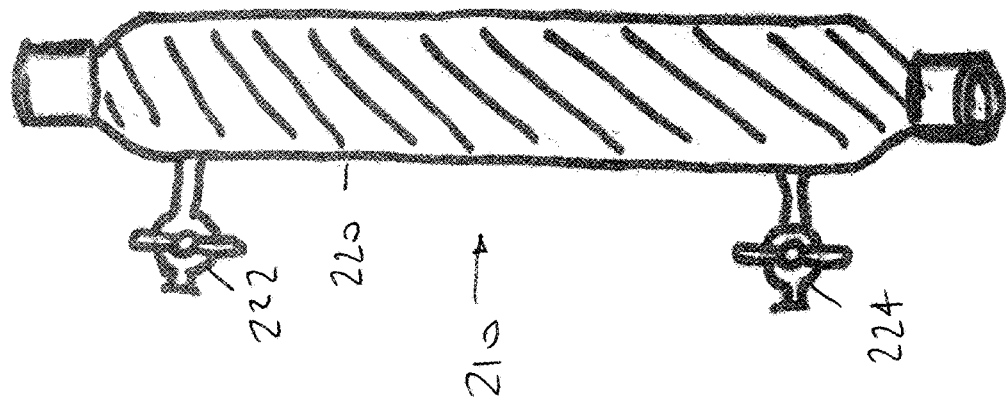
FIG. 4B is a side view of a flushing device that may be used to flush a medical device therein, e.g., using the flushing system of FIG. 4A.
Figure 4A:
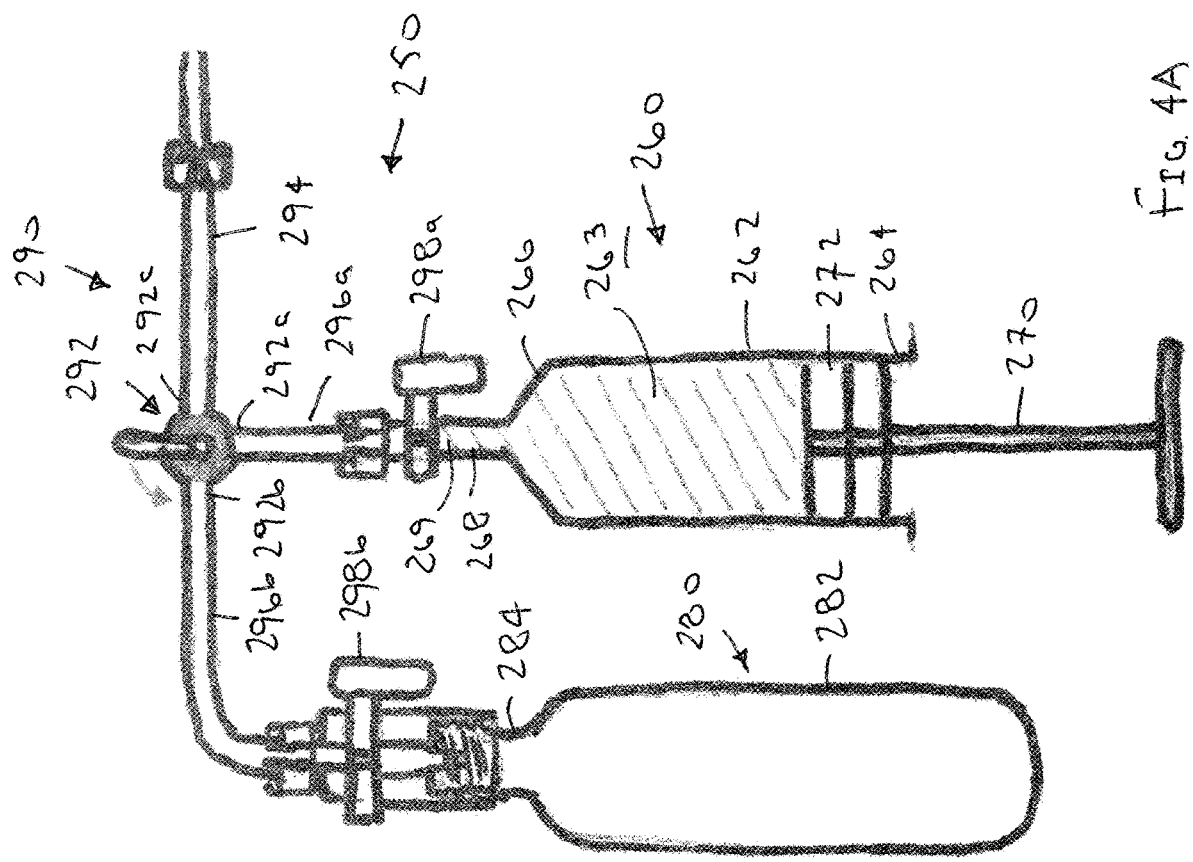
FIG. 4A is a side view of a flushing system that may be used to sequentially flush a medical device with perfluorocarbon and another fluid.

The delivery line 290 includes a stop-cock 292 including two inlets 292a, 292b, and an outlet 292c coupled to delivering tubing 294, which may be coupled to a device to be flushed, such as the flushing device 210 shown in FIG. 4B. The inlets 292a, 292b are coupled to tubing 296a, 296b that are, in turn, coupled to the syringe 260 and source 280, respectively. Optionally, the tubing 294, 296 may include one or more connectors, e.g., Luer fittings, and the like, that allow ends of the tubing 294, 296 to be removably coupled to the stop-cock 292, the syringe 260, the source 280, and/or the device to be flushed.

Optionally, as shown, the syringe 260 and source 280 may include individual stop-cocks 298a, 298b, e.g., coupled to the hub 268 and outlet 284, respectively. The stop-cocks 298 may be integrally formed with the respective devices or may be separate fittings that are connected to the respective devices. For example, as shown, the stop-cock 298a is integrally formed in the hub 268 of the syringe 260, while the stop-cock 298b is attached to the outlet 284 of the source 280, e.g., by one or more of an interference fit, cooperating threads, bonding with adhesive, and the like.

Using the flushing device 210 as an example, the free end of the delivery tubing 294 may be coupled to an inlet port 222 of the housing 220 of the flushing device 210, which may contain a device intended for introduction into a patient's body (not shown), stent-grafts, stents, vascular and neurovascular coils, covered and uncovered occluders, embolic protection devices and filters, heart valves, valve repair and augmentation prostheses, other prostheses, and the respective delivery systems for such devices, as described elsewhere herein. Exemplary embodiments of the flushing device 210 are described in International Publication No. WO 2017/072592, the entire disclosure of which is expressly incorporated by reference herein.

The flushing line 290 may then be used to sequentially flush the device 210 (and prosthesis therein) using a desired sequence without having to disconnect and/r reconnect the different sources of flushing fluid. In an exemplary procedure, first, the source 280 may be opened (by opening stop-cock 298b) and the delivery stop-cock 292 directed to a first position communicating with tubing 296b to deliver gas, e.g., carbon dioxide, from the source 280 into the device 210 via the delivery line 294. Optionally, the delivery line 294, stop-cock 292, etc. may be initially flushed with the gas before connecting the delivery line 294 to the inlet port 222, if desired.

After the device 210 has been flushed with the gas from the source 280, the stop-cock 292 may be directed to a second position communicating with tubing 296a to deliver PFC from the syringe 260. For example, the syringe stop-cock 298a may be opened, and the plunger 270 advanced to direct PFC from the interior 263 through the tubing 296a, 294 into the device 210. It will be appreciated that the flushing fluid directed into the device 210 may be removed, along with any remaining air or gas within the device 210, via outlet port 224.

In this sequence, carbon dioxide from the source 280 may be used to initially flush air from the device 210, and then PFC may be used to remove the carbon dioxide within the device 210, similar to the methods described elsewhere herein.

Optionally, one or more additional sources of flushing fluid (not shown) may be provided in the delivery line 290, e.g., coupled to the stop-cock 292 at another position, or provided in one of the tubing lines with a second stop-cock (also not shown). In this manner, the necessary stop-cocks may be directed to positions to selectively deliver one of the flushing fluids in a desired sequence.

It will be appreciated that the systems and methods herein may be used to flush and/or otherwise remove air from other devices before introduction into a patient's body. For example, a catheter, sheath, or other tubular device carrying a stent, coil, or other prosthesis or implant, may be flushed using any of the systems and methods described herein. In addition, it will be appreciated that the systems and methods herein may be used to flush and/or otherwise remove air from devices after introduction into a patient's body. Given the high solubility of air and other gases within perfluorocarbon liquid solutions, flushing with perfluorocarbon may more than mechanically thrive the air or gases from the device, but the chemical and/or physical properties of the fluorocarbon may dissolve and absorb the air or gases into the solution, thereby preventing their exposure or release within a patient's body.

In addition, it will be appreciated that stent-grafts, stents, or other prostheses may be exposed to perfluorocarbon solutions and/or sequences of gases and/or solutions, as described above, using other methods than flushing. For example, a prosthesis may be immersed in a perfluorocarbon solution, e.g., within a flushing and/or loading device, similar to those described in U.S. provisional application Ser. No. 62/247,287, filed Oct. 28, 2015, the entire disclosure of which is expressly incorporated by reference. In this method, the prosthesis may be inserted into the flushing device and one or more solutions and/or gases may be introduced into the device to remove air from the prosthesis. The prosthesis may then be loaded into a delivery device, which itself may also be flushed before and/or after loading the prosthesis.

In another application, valve prostheses, e.g., transcatheter aortic valves, pulmonary or mitral valve prostheses, and other structural heart repair devices delivered via catheter may be flushed using the systems and methods herein. For example, a transcatheter aortic valve may be submerged in PFC solution in their relaxed, expanded state, and then may be compressed and/or loaded into a delivery catheter. Once loaded, additional sequences of flushing, e.g., involving carbon dioxide, PFCs, and/or saline, may be used to further remove air from the device before introduction into a patient's body. The systems and methods herein may also be used to flush other devices before introduction into a patient's body, e.g., occlude devices, filters, and the like.

Optionally, in any of the systems and methods herein, vibration energy, e.g., ultrasound or other frequencies of shaking or vibration, may be used to enhance absorption of air or other gases. For example, PFC may be introduced into a flushing device or delivery device containing a prosthesis, and then an ultrasound probe may be placed around or otherwise against the device and ultrasonic energy delivered to shorten the contact phase of the PFC.

In addition or alternatively, if desired, the PFC solution may be cooled or heated to a desired temperature, e.g., between about zero and ten degrees Celsius (0-10° C.), to enhance absorption of air or other target gas by the PFC solution.

In addition, PFCs may also be used during packaging and/or other preparation of a medical device, e.g., under air-free room conditions. For example, as described above, a valve prosthesis may be immersed in a PFC solution in its relaxed and/or deployed configuration, and then compressed into a delivery configuration and loaded into a catheter or other delivery device. The device may then be packaged under conditions in which the device is sealed in a gas-tight package. The PFC solution may remain within the device when packaged or may be removed under vacuum. The packaged device may then be processed further as necessary, e.g., sterilized using e-beam sterilization or other known procedures.

Alternatively, after flushing with PFC, the medical device may be flushed with carbon dioxide or other bio-inert gas, and then packaged in a gas-tight package. Given that carbon dioxide is heavier than air, the device may be stored in the package such that carbon dioxide remaining within the device and package would reduce the risk of air entering the package and/or device.

In any of these embodiments, immediately before, use, the package may be opened, and the device removed and/or otherwise prepared before the procedure. If desired, the device may be flushed again with saline, carbon dioxide and/or other bio-inert gas, or with PFC, e.g., in a single flushing step or a sequence of steps, similar to other embodiments herein. Using PFC to flush and/or package the device or using PFC/carbon dioxide may reduce the amount and/or time to flush and/or otherwise prepare the device before introduction into a patient's body.

In accordance with another embodiment, solutions including perfluorocarbons may be used for other purposes in addition to flushing medical devices. For example, balloon catheters include an inflation lumen communicating between a port in a hub or handle of the device and an interior of the balloon. In one embodiment, a source of perfluorocarbon may be coupled to the hub and used to flush air or other gases from the inflation lumen and/or the interior of the balloon, e.g., during manufacturing or immediately before use, e.g., alone or in combination with other flushing sequences, such as those described elsewhere herein.

For example, before use, a PFC solution may be introduced into the inflation lumen, e.g., using a syringe similar to the syringes 160, 160' shown in FIGS. 3A and 3B, to flush the inflation lumen and interior, e.g., thereby inflating the balloon. The solution may then be removed from the interior and inflation lumen, e.g., by withdrawing the plunger 170 from the syringe 160, 160' and/or applying a source of vacuum, thereby collapsing the balloon and removing the solution from the interior and inflation lumen. In this manner, any residual air or other gas may be absorbed by the solution and/or otherwise removed from the inflation lumen and balloon. Optionally, thereafter, the inflation lumen may then be flushed with another fluid, e.g., saline, if desired. In another option, the PFC solution and/or subsequent saline may be used to at least partially fill the inflation lumen to prevent air from returning therein during subsequent preparation and/or use.

In addition, a source of perfluorocarbon, such as the syringes 160, 160,' may be used during a procedure to inflation a balloon after introducing the catheter into a desired location within a patient's body. For example, rather than using saline and/or contrast, the PFC solution may be delivered in a similar manner into the inflation lumen to expand the balloon within the patient's body, e.g., within the patient's heart or vasculature. Thus, if the balloon were to rupture, the PFC solution (and any residual air bubbles captured therein) would be released within the patient's body, rather than air and conventional flushing solution, thereby reducing the risk of embolism or other injury to the patient. Such use of PFC as inflation media may be particularly useful for coronary or neurological balloons, where air may cause myocardial infarction, arrhythmia, or embolism.

Optionally, the PFC solution may be radiopaque, if desired, e.g., where the balloon is monitored using fluoroscopy or other external imaging. For example, Perflubron or other radiopaque fluorocarbon may be used in such applications. Alternatively, a radiolucent PFC may be used, such as Perfludecaline, where it is not desired to have the balloon appear under fluoroscopy, e.g., when the catheter includes other radiopaque markers.

Using PFCs to flush and/or inflate balloons may provide one or more advantages over conventional systems, such as using saline solutions and/or vacuum to de-air an inflation lumen and balloon. For example, the viscosity of the PFC solution may facilitate rapid infusion and/or aspiration of the solution during expansion and/or collapse of the balloon. For example, PFCs may have a lower viscosity compared to contrast and/or other materials that may be added to saline or other inflation media. In addition, using de-gassed PFC may render saline flushing or other flushing unnecessary or may reduce the time needed to effectively de-air an inflation lumen and/or balloon. Further, de-gassed PFC may absorb any residual air that may be trapped within the device during flushing and/or use within the patient's body.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A system for flushing target gas from a medical device, comprising:
    an elongate delivery device comprising a proximal end, a distal end, a lumen extending between the proximal and distal ends, and a port on the proximal end communicating with the lumen;
    a balloon carried by the delivery device;
    a source of perfluorocarbon solution connectable to the port for flushing the lumen with the solution to remove target gas from one or both of the balloon and the lumen, wherein the perfluorocarbon comprises one of perflubron, perfluorodecaline, perfluorotributylamine, perfluorohexane, perfluorononane, perfluoropentane, perfluorodichlorooctane, and perfluoro-15-crown-5-ether; and
    a source of gas comprising one of carbon dioxide and a bio-inert gas connectable to the port for flushing the lumen with flushed gas to remove target gas from one or both of the balloon and the lumen.

2. A system for flushing target gas from a medical device, comprising:
    an elongate delivery device comprising a proximal end, a distal end, a lumen extending between the proximal and distal ends, and a port on the proximal end communicating with the lumen;
    a balloon carried by the delivery device; and
    a source of perfluorocarbon solution connectable to the port for flushing the lumen with the solution to remove target gas from one or both of the balloon and the lumen,
    wherein the perfluorocarbon comprises one of perflubron, perfluorodecaline, perfluorotributylamine, perfluorohexane, perfluorononane, perfluoropentane, perfluorodichlorooctane, and perfluoro-15-crown-5-ether, and
    wherein the source of perfluorocarbon solution comprises degassed perfluorocarbon, an emulsion including perfluorocarbon, a radiopaque perfluorocarbon, or a combination thereof.

3. A system for flushing target gas from a medical device, comprising:
    an elongate delivery device comprising a proximal end, a distal end, a lumen extending between the proximal and distal ends, and a port on the proximal end communicating with the lumen;
    a balloon carried by the delivery device;
    a source of perfluorocarbon solution connectable to the port for flushing the lumen with the solution to remove target gas from one or both of the balloon and the lumen, wherein the perfluorocarbon comprises one of perflubron, perfluorodecaline, perfluorotributylamine, perfluorohexane, perfluorononane, perfluoropentane, perfluorodichlorooctane, and perfluoro-15-crown-5-ether; and
    a source of degassed saline connectable to the port for flushing the lumen with the degassed saline to remove target gas from one or both of the balloon and the lumen.

4. A method for removing gas from a medical device, comprising:
    providing a source of perfluorocarbon; and
    exposing the medical device to perfluorocarbon from the source of perfluorocarbon to remove target gas from the medical device, wherein the medical device comprises a balloon.

5. The method of claim 4, wherein the medical device is exposed to the perfluorocarbon before the medical device is introduced into a patient's body.

6. The method of claim 4, wherein the source of perfluorocarbon contains degassed perfluorocarbon.

7. The method of claim 4, wherein the source of perfluorocarbon comprises an emulsion including perfluorocarbon.

8. A method for flushing a balloon device including a balloon, comprising:
    introducing a solution comprising perfluorocarbon into an interior of the balloon for a time sufficient to remove a quantity of target gas from the interior;
    removing the solution from the interior.

9. The method of claim 8, wherein the balloon is collapsed to an uninflated state when the solution is removed, the method further comprising introducing the balloon into a patient's body in the uninflated state.

10. The method of claim 8, wherein the balloon device comprises a tubular member including an inflation lumen communicating with the interior of the balloon, and wherein the solution is introduced into the interior via the inflation lumen.

11. The method of claim 8, further comprising flushing the interior one or more times with an additional fluid before or after introducing and removing the solution.

12. The method of claim 9, further comprising inflating the balloon in a desired location within the patient's body using the solution comprising perfluorocarbon.

13. The method of claim 9, further comprising inflating the balloon in a desired location within the patient's body using a second solution comprising perfluorocarbon.

14. The method of claim 13, wherein the second solution comprising perfluorocarbon comprises a degassed perfluorocarbon, a radiopaque perfluorocarbon, an emulsion including perfluorocarbon, or a combination thereof.

15. The method of claim 12, wherein the solution comprising perfluorocarbon comprises a degassed perfluorocarbon, a radiopaque perfluorocarbon, an emulsion including perfluorocarbon, or a combination thereof.

16. The method of claim 8, wherein the solution comprising perfluorocarbon comprises a degassed perfluorocarbon, a radiopaque perfluorocarbon, an emulsion including perfluorocarbon, or a combination thereof.

17. A system for flushing target gas from a medical device, comprising:
    an elongate delivery device comprising a proximal end, a distal end, a lumen extending between the proximal and distal ends, and a port on the proximal end communicating with the lumen;
    a balloon carried by the delivery device; and
    a source of perfluorocarbon solution connectable to the port for flushing the lumen with the solution to remove target gas from one or both of the balloon and the lumen, wherein the perfluorocarbon comprises one of perflubron, perfluorodecaline, perfluorotributylamine, perfluorohexane, perfluorononane, perfluoropentane, perfluorodichlorooctane, and perfluoro-15-crown-5-ether, wherein the system comprises a second source of perfluorocarbon solution connectable to the port for inflating the balloon, and wherein the second source of perfluorocarbon solution comprises a degassed perfluorocarbon, a radiopaque perfluorocarbon, an emulsion including perfluorocarbon, or a combination thereof.

* * * * *